United States Patent [19]

Errico et al.

[11] Patent Number: 5,925,047
[45] Date of Patent: Jul. 20, 1999

[54] COUPLED ROD, ANTERIOR VERTEBRAL BODY SCREW, AND STAPLE ASSEMBLY

[75] Inventors: Joseph P. Errico, Far Hills; Thomas J. Errico, Summit; James D. Ralph, Oakland, all of N.J.

[73] Assignee: Third Millennium Engineering, LLC, Summit, N.J.

[21] Appl. No.: 09/174,960

[22] Filed: Oct. 19, 1998

[51] Int. Cl.[6] .................................................. A61B 17/58
[52] U.S. Cl. ............................... 606/65; 606/61; 606/69; 606/72; 606/73
[58] Field of Search .................. 606/60, 61, 65, 606/69, 70, 72, 73, 75

[56] References Cited

U.S. PATENT DOCUMENTS

| | | | |
|---|---|---|---|
| 5,415,659 | 5/1995 | Lee et al. | 606/61 |
| 5,620,443 | 4/1997 | Gertzbein et al. | 606/73 |
| 5,662,652 | 9/1997 | Schafer et al. | 606/73 |
| 5,690,629 | 11/1997 | Asher et al. | 606/75 |
| 5,713,898 | 2/1998 | Stucker et al. | 606/61 |
| 5,810,816 | 9/1998 | Roussouly et al. | 606/61 |

Primary Examiner—Michael Buiz
Assistant Examiner—Daphna Shai
Attorney, Agent, or Firm—Joseph P. Errico, Esq.

[57] ABSTRACT

A rod, screw, and staple assembly for use in conjunction with anterior or lateral spinal rod implant apparatus includes a screw having a vertebral body screw which has a shaft which is insertable into a vertebral bone and a head portion which includes a rod receiving channel and a radially extending flange. The vertebral body staple includes a flat portion which has a hole through it. The hole has a rim which is upwardly extending and a concave recess formed in the underside of the flat portion around the hole. The staple also includes several barbs which independently hold the staple to the bone surface to which it is to be affixed. The screw is first inserted into the vertebral bone, and then the staple is mounted over the head portion of the screw, such that the head extends above the annular rim. The rod is then inserted into the rod receiving channel and seats against the uppermost surface of the annular rim. The application of a top locking nut onto the head of the screw causes the rod to compress against the staple, the barbs of which are driven into the vertebral bone, and the staple is further compression locked to the screw.

8 Claims, 3 Drawing Sheets

COUPLED ROD, ANTERIOR VERTEBRAL BODY SCREW, AND STAPLE ASSEMBLY

BACKGROUND OF THE INVENTION

1. Field of the Invention

This invention relates generally to a spinal rod fixation apparatus having an elongate rod, a vertebral body screw, and a stabilizing staple element, and more particularly to a rod, screw and staple assembly which is selectively lockable in combination to provide enhanced stability and bone holding strength.

2. Description of the Prior Art

The spinal column is highly complex system of bones and connective tissues which houses and protects critical elements of the nervous system and the arterial and veinous bodies in close proximity thereto. In spite of these complexities, the spine is a highly flexible structure, capable of a high degree of curvature and twist through a wide range of motion.

Genetic or developmental irregularities, trauma, chronic stress, tumors, and disease, however, can result in spinal pathologies which either limit this range of motion, or which threaten the critical elements of the nervous system housed within the spinal column. A variety of mechanical implant structures have been disclosed in the art which are used during surgical intervention to immobilize segments of the spine which are either unstable or have, in combination, become so irregular that they threaten the continued health of the patient. These assemblies are generally classified as anterior, posterior, or lateral. As the classifications suggest, posterior implants are attached to the back of the spinal column, generally hooking under the lamina and entering into the central canal, attaching to the transverse process, or coupling through the pedicle bone using pedicle screws. Posterior fixation assemblies using such screws are generally used in short sequence immobilization indications, and generally in the larger, lower lumbar bones, for their attending pathologies. Lateral and anterior assemblies, by contrast are coupled to the anterior portion of the spine, which is the sequence of vertebral bodies, and are often used throughout long segments of lumbar and thoracic sequences of vertebrae. A specific pathology which often requires significant surgical intervention along extended numbers of vertebrae is scoliosis. The present invention relates to spinal fixation devices for immobilizing and altering the alignment of the spine over a large number, for example more than three or four, vertebra by means of affixing at least one elongate rod to the sequence of selected vertebral bodies.

Anterior (and/or lateral) "rod assemblies" of the prior art have generally been inserted into the bone either unicortically or bicortically, wherein the shaft of the screw transects (and gains fixation strength as it passes through) one or two exterior layers of the vertebral bone, respectively. Exposing the tip of the screw shaft through the opposing side of the bone's exterior surface does, however, entail a risk inasmuch as important blood vessels, nerve roots, as well as other critical tissues are often in jeopardy of injury through contact with an exposed screw tip. Bicortical fixation, however, provides greatly enhanced strength against pullout; an event in which the screw is pulled free of the bone as its grip inside the vertebra fails to hold.

In order to provide enhanced stability against such pullout events, a staple as shown in FIG. 1, was designed. The basic staple of the prior art comprises a flat metal surface 10 having a hole 12 formed in the center thereof. The corners 14 of the staple 10 are curved downwardly to form four spaced apart spikes. The basic vertebral body screw 20, rod 30 and top locking nut 40 of the prior art are shown in FIG. 2, in conjuction with the staple 10, in an exploded assembly diagram. The screw 20 is inserted through the hole 12 in the staple 10 until the wider top, rod receiving portion 22 of the screw, contacts and seats in the hole 12 of the staple. The wider base, provided by the staple 10, impairs toggling action by the screw within the bone, and is intended to prevent motion which can cause the screw to bone interface from breaking down. The rod 30 is then placed in the rod receiving channel 24 of the screw head 22, and a top locking nut 40 is advanced onto the top of the screw head 22, thereby locking the rod to the screw 20, and by association, to the bone.

In some advanced embodiments of this screw and staple design (not shown), the hole and the bottom of the screw are designed such that the screw may be inserted at a modest angle to the staple, thus permitting stable seating of the screw and staple, despite slight offsets of the screw relative to the bone surface.

These screw and staple assemblies of the prior are, however, do not prevent the most frequent pullout failure mechanism, which is direct vertical force pullout which is caused when the rod itself imparts a sufficient stress against the shaft to cause the screw to back out of the hole. In addition, the ability of the staple to impair toggling of the screw in the bone is limited insofar as the screw and staple are not held together by any specific means, and therefore does not prevent the screw from rotating in the hole and causing microfractures, which can lead to bone failure. Further, the prior art designs limit the ability of the rod receiving head of the screw to be properly aligned with the rod. In many instances, the screw is not fully seated in the hole of the staple because the screw had to be backed out of the hole by the surgeon to align the rod in the rod receiving channel of the head.

It is, therefore, the principal object of the present invention to provide a vertebral body screw, rod, and staple assembly which provides enhanced stability and pullout protection.

In addition, it is an object of the present invention to provide such an assembly which includes a stable locking of the staple to the screw so that the screw head can be positioned in the ideal orientation without risking the union of the screw and staple.

Accordingly it is also an object of the present invention to provide an assembly which the staple and screw are lockably coupled together upon completion of the implantation.

It is also a principal object of the present invention to provide a reliable, durable, and efficient, long term fixation assembly for spine stabilization.

Other objects of the present invention not explicitly stated will be set forth and will be more clearly understood in conjunction with the descriptions of the preferred embodiments disclosed hereafter.

SUMMARY OF THE INVENTION

The preceding objects of the invention are achieved by the present invention which is a vertebral body staple, screw and rod assembly, having enhanced stability and pullout strength, in which the staple, the rod and the screw head may be locked together to form a reliable fixation to the vertebral bone. More particularly, the assembly of the present invention comprises a vertebral body screw having a head which is formed with a rod receiving channel, a rod, a locking means for engaging the head of the screw and locking a rod in the rod receiving channel of the head, and a vertebral body staple which engages the vertebral bone and the screw head in such a way that the action of locking the rod in the rod receiving channel further locks the staple to the screw and the entire assembly to the vertebral bone.

The vertebral body screw of the present invention comprises a shaft and a head. The shaft portion of the screw is designed to be inserted into the vertebral bone, and to firmly anchor the screw to the bone. This fixation is generally enhanced by the shaft including a threading which engages the bone material along its length and prevents axial translation of the shaft along the length of the hole in the bone into which it has been advanced. The head of the screw includes a rod receiving channel which may alternatively be formed vertically in the top of the head or laterally in the side of the head. More particularly, both types of rod receiving channel admit the rod into the head such that the rod extends perpendicularly to the axis of the screw, but in the first instance (the vertical channel), the channel is formed between two upright extending members, and in the second (the lateral channel), the channel is formed in the side of the head. In each embodiment, the upper portion of the head (either the upper portion of the upright extending members or the portion of the head directly above the lateral channel) includes a threading for receiving thereon a top locking nut, or other means for securing a rod within the channel.

The lower portion of the head further includes an engaging surface which is designed to mate with the staple at a variety of different angles. This engaging surface, which shall be explained in greater detail with respect to the assembly of the screw and the staple, generally comprises an annular flange extending outwardly from the exterior surface of the head. The flange is rounded to present a convex section of a sphere to permit engagement with a concave recess which is formed in the vertebral body staple, as more fully explained hereinbelow.

The vertebral body staple comprises a member having a flat portion and a plurality of downwardly directed protuberances, generally shaped like spikes or barbs, which extend perpendicularly to the plane formed by the flat portion. The flat portion further includes a hole formed in the center thereof. The hole has a cylindrical rim which is extended upwardly, such that the hole has a cylindrical appearance. This upwardly extending annular rim has a generally constant diameter along its length, however, the bottom portion of the rim is concavely tapered outwardly such that the undersurface of the staple includes a recess around the hole. This concave taper is designed to mate with the curved annular flange of the head of the screw.

More particularly, the head of the screw is designed such that the staple may be placed over it, and the upper portion thereof, into which the rod is inserted, extends through the hole and partially beyond the upwardly extending rim. The upper surface of the rim, however is designed to intially seat above the lower surface of the rod receiving channel such that a rod placed in the channel rests on the upper surface of the rim, and not on the lowermost surface of the channel.

The surgical assembly of the present invention is provided as follows. First, the vertebral body surfaces are exposed and prepared to receive the screws (one at each bone). The screws are advanced into the bones at the appropriate angles and to the desired height. The staples are then placed over the screws such that the heads of the screws extend through the holes in the staples, and the upwardly extending rims of the holes are positioned above the lowermost surfaces of the channels. The rod is then placed into the channels of the screw heads, extending along the length of the spinal sequence which is to be immobilized. The locking means, for example a locking nut, is then advanced onto the engaging means of the screw head to secure the rod in the channel. The advancement of the rod into the channel by the locking nut, or other such means, causes the staple to be pushed downward along the lower portion of the screw head, and simultaneously, the compression of the bone fixation elements of the staple into the bone. This advancement of the rod and staple are halted when the lower concave surface around the hole in the staple engages the convex annular flange of the head. The compressive force of the nut against the rod, and the rod against the staple, and the staple against the head of the screw firmly locks the assembly together and to the vertebral bone.

It shall be understood that the rounded surfaces of the lower portion of the hole in the staple and the annular flange of the head of the screw permit the head and the staple to be angularly offset relative to one another without compromising the ideal coupling of the two elements, nor the ideal alignment of either the staple or the screw with the bone.

DETAILED DESCRIPTION OF THE PREFERRED EMBODIMENT

While the present invention will be described more fully hereinafter with reference to the accompanying drawings, in which particular embodiments and methods of implantation are shown, it is to be understood at the outset that persons skilled in the art may modify the invention herein described while achieving the functions and results of this invention. Accordingly, the descriptions which follow are to be understood as illustrative and exemplary of specific structures, aspects and features within the broad scope of the present invention and not as limiting of such broad scope.

Figure 1:
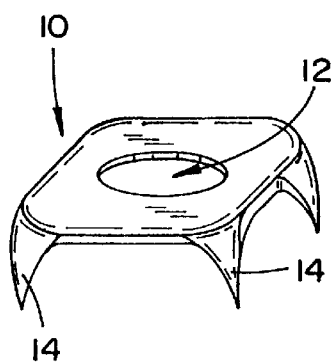
FIG. 1 is a side perspective view of a vertebral body staple of the prior art.
Figure 2:
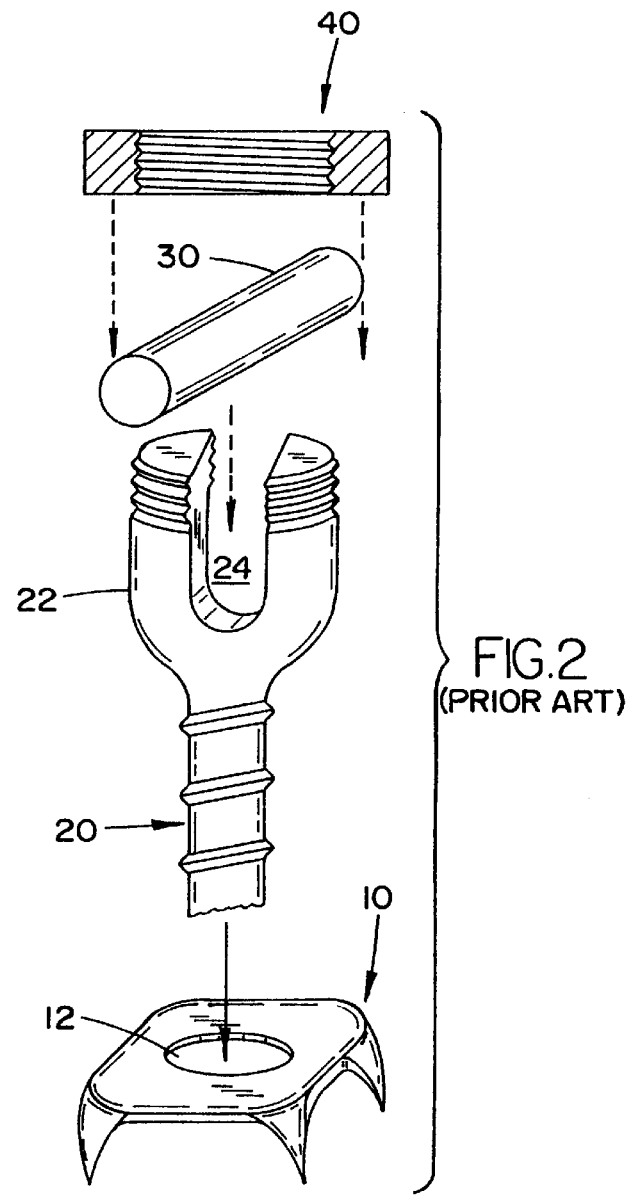
FIG. 2 is an exploded assembly view of a staple, vertebral body screw, rod and top locking nut of the prior art.
Figure 3:
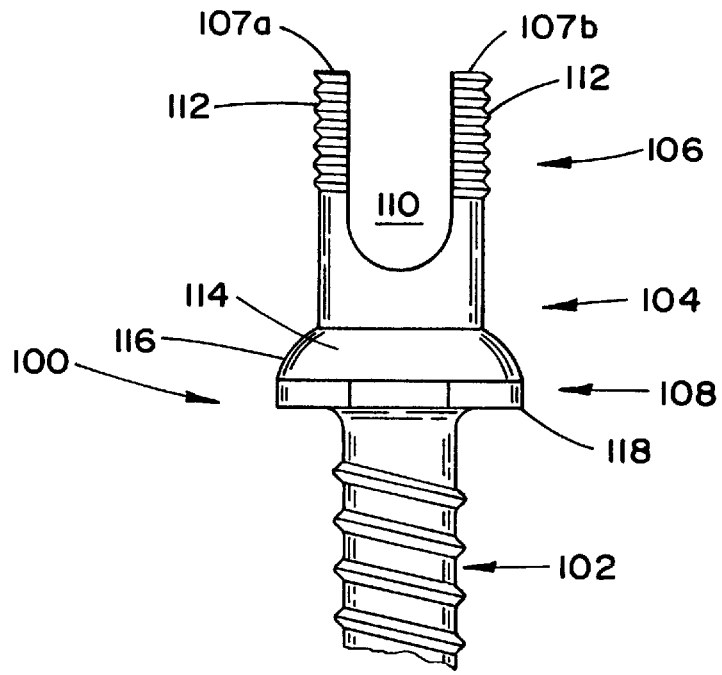
FIG. 3 is a side view of a vertebral body screw which is an aspect of the present invention.

Referring now to FIG. 3, a side view of a vertebral body screw 100 of the present invention, comprising a shaft and a rod coupling head, is shown. The screw 100 comprises a shaft 102, which is threaded, and a head portion 104 having an upper portion 106 and a lower portion 108. The threading of the shaft is preferably of the type which is suited for high engagement with bone materials, as are well known in the art. It shall be understood that a variety of shaft designs are interchangeable with the present design. The specific choice of shaft features, such as thread pitch, shaft diameter to thread diameter ratio, and overall shaft shape, should be made be the physician with respect to the conditions of the individual patient's bone, however, this invention is compatible with a wide variety of shaft designs.

The upper portion 106 of the head 104 comprises a pair of upwardly extending members 107a, 107b which define therebetween a rod receiving channel 110. The uppermost exterior surfaces of the upwardly extending members 107a, 107b include a threading 112 which is ideally suited for receiving a locking nut (as set forth more particularly with respect to FIG. 5). In alternative designs (not shown), which were introduced above, it is possible to design the rod receiving channel 110 into the side of the upper portion 106 of the head 104, however, the preferred embodiment includes the rod receiving channel 110 in a vertical alignment.

The lower portion 108 of the head 104 comprises an annular flange 114 which extends laterally outward from the axial body of the screw 100. This flange 114 is rounded such that the upper surface 116 thereof has an overall continuous concave profile, which is in fact a section of a sphere. In preferred embodiments, the exterior perimeter 118 of the flange 114 comprises a hexagonal design such that the screw 100 may be advanced into a bone by means of a torque applying socket means. Alternative means for inserting the screw into the vertebral bone may include screwdriver recesses in the trough of the rod receiving channel 110, or other such suitable combinations.

Figure 4:
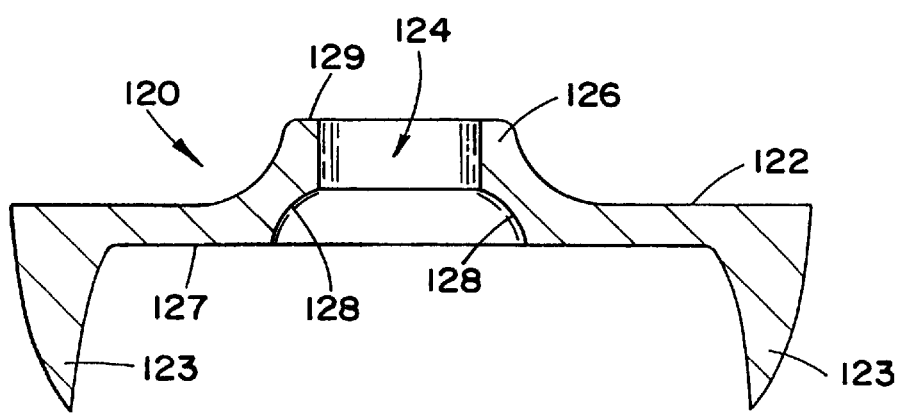
FIG. 4 is a side cross-sectional view of a vertebral body staple which is an aspect of the present invention.

Referring now also to FIG. 4, the vertebral body staple 120 of the present invention is provided in a side cross section view. The staple 120 includes a flat surface 122 and a plurality of downwardly directed barbs 123, disposed at the lateral edges of the flat portion 122. The barbs 123, which are intended to be inserted into the vertebral bone surface to provide fixation of the staple to the bone, extend perpendicularly downward from the plane formed by the flat portion 122. The flat portion 122 further includes a hole 124 formed in the center thereof. The hole 124 has a cylindrical rim 126 which extends upwardly from the flat surface. This upwardly extending annular rim 126 has a generally constant diameter along its length, however, the bottom portion of the rim is concavely tapered outwardly such that the undersurface 127 of the staple includes a recessed surface 128 around the hole 124.

Figure 5:
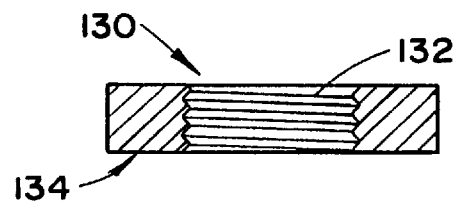
FIG. 5 is a side cross-section view of a top locking nut which is an aspect of the present invention.

Referring now to FIG. 5, a top locking nut 130 of the present invention is provided in a side cross section view. The nut 130 comprises a standard threaded nut design, having an interior threading 132 which is matable and advanceable along the exterior threading 112 of the upper portion 104 of the vertebral body screw 100. The exterior surface 133 of the nut 130 is ideally suited for engagement and advancement along the threading 112 of the head 104 of the screw 100 by means of a standard torque applying instrument, such as having a series of flats for engaging a wrench or socket. The lower surface 134 of the nut 130 is flat, thus providing maximal surface area over which the downward locking force applied by the nut may be borne.

Figure 6:
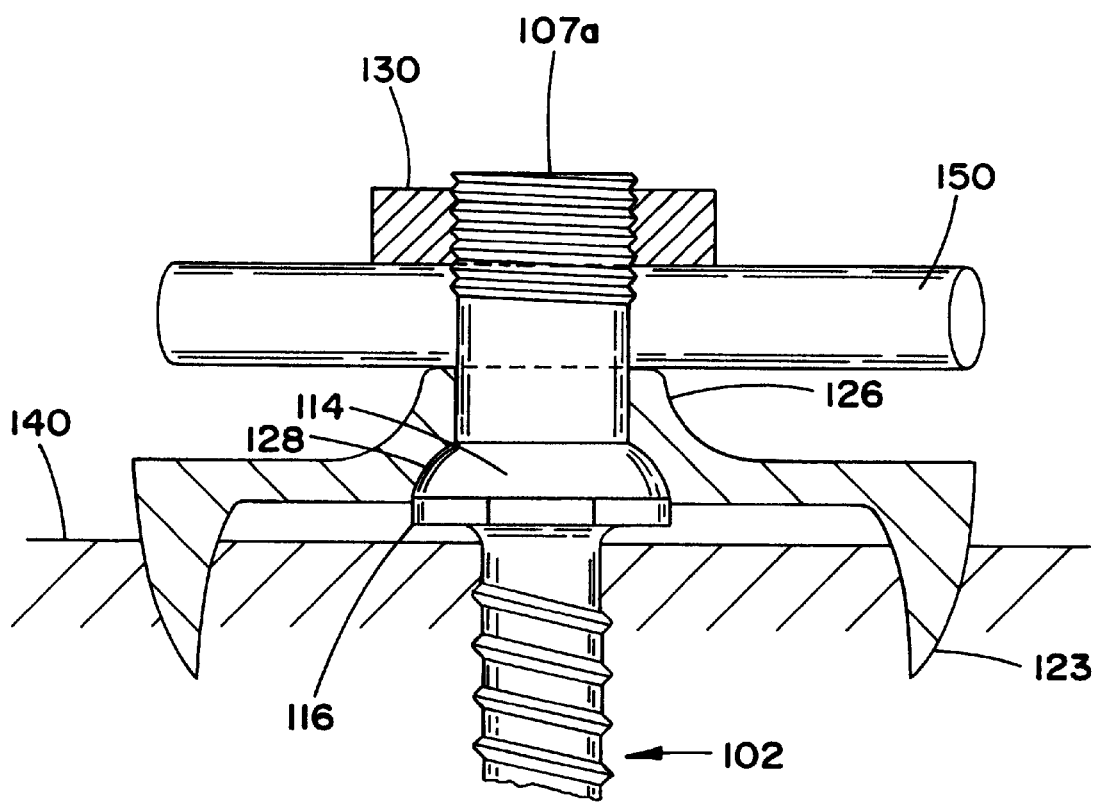
FIG. 6 is a side cross section view of a fully assembled embodiment of the present invention.

Referring now to FIG. 6, a completely assembled embodiment of the present invention is provided in a side cross section view, this view being taken along a direction in which the screw 100 is rotated about its elongate axis by 90 degrees from the orientation illustrated in FIG. 3. The implantation of this device, as well as its functionality and advantages shall be explained in conjunction with the description of the elements and workings set forth in this Figure. The screw 100 is implanted into the vertebral bone such that the head 104, that is both the upper and lower portions 106, 108 of the screw are exposed above the bone surface (hereinafter identified as 140). The screw 100 may be implanted into the bone at a variety of angles within a range of angles including perpendicular and non-perpendicular angles relative to the bone surface 140. The staple 120 is then mounted over the screw head 104 such that the upper portion 106 of the screw 100 extends through the hole 124 in the flat portion 122 of the staple 120. The upper surface 129 of the annular rim 126 of the hole 124 will be positioned above the bottom of the rod receiving channel 110 (because the height of the rim is greater than the height of that portion of the head). The barbs 123 of the staple are then inserted by force into the vertebral bone surface 140 as deeply as possible (the deppest possible insertion being the point at which the recess 128 in the bottom of the staple 120 seats against the convex upper surface 116 of the flange 114. Because of the spherical interface between the recess 128 and the convex surface 116 of the flange, so long as the hole 124 is of sufficient diameter, the screw 100 and the staple 120 may be oriented in non-perpendicular alignments, however, in the preferred embodiments, this freedom of angulation is minimized to prevent the rod from being unstably mounted in the rod receiving channel 110 and on the upper surface of the rim 124.

Once the staple 120 and screw 100 have been properly positioned, the rod 150 is inserted into the rod receiving channel 110, and seats against the upper surface 129 of the annular rim 125. The subsequent application of the top locking nut 130 onto the upwardly extending members 107a,107b of the head 104 of the screw 100, and it is advanced downwardly, there is a compressive force applied to the rod 150 by the lower surface 134 of the nut 130. The rod 150 then applies a pressure against the staple 120, the barbs 123 of which are further compressed into the bone 140, and the flange 114 of the screw 100 and recessed undersurface 128 of the staple 120 are locked together. Thus the staple 120, the rod 150, the screw 100, and the vertebral bone are stably fixed together. This assembly strongly prevents screw pullout failure of the rod immobilization construct by providing a wider base of fixation strength for anchoring to the bone, as well as preventing rotational and angular motion of the screw which has the effect of breaking the grip of the threaded shaft 102 in the bone.

While there has been described and illustrated embodiments of a rod, vertebral body screw and staple assembly for use with anterior or lateral spinal rod implantation apparatus, it will be apparent to those skilled in the art that variations and modifications are possible without deviating from the broad spirit and principle of the present invention. The present invention shall, therefore, be limited solely by the scope of the claims appended hereto.

We claim:

1. A vertebral body screw and staple assembly for use with orthopedic rod implantation apparatus, comprising:

a vertebral body staple having first and second portions thereof, said first portion including means for direct fixation of the staple to vertebral bone, said second portion having a throughhole formed therein wherein the throughhole includes an annular rim which is upwardly extending, and an undersurface which forms a concave recess around the throughhole;

a vertebral body screw having a shaft which is insertable into a vertebral bone and a head portion which includes a rod receiving channel;

means for securing a rod in said rod receiving channel;

said throughhole of said staple being mountable about the head portion of said screw, such that the insertion of said screw into a vertebral bone, the mounting of the staple about the head of the screw, the insertion of a rod in said rod receiving channel, and the application of said means for securing the rod in the rod receiving channel causes the screw, the staple, and the rod to be locked together in a fully secured combination which is securely fixed to the vertebral bone.

2. The vertebral body screw and staple assembly as set forth in claim 1, wherein said means for direct fixation of the staple to vertebral bone comprises a plurality of downwardly extending barbs.

3. The vertebral body screw and staple assembly as set forth in claim 1, wherein said vertebral body screw further includes a laterally extending convex flange which mates with the concave recess formed in the undersurface of the staple.

4. The vertebral body screw and staple assembly as set forth in claim 3, wherein the annular rim of the staple extends above a lowermost surface of the rod receiving channel, such that when the staple is mounted about the head of the screw, and the rod is inserted into the rod receiving channel, the rod seats on an upper surface of the annular rim.

5. The vertebral body screw and staple assembly as set forth in claim 4, wherein the screw, the staple, and the rod are locked together in a fully secured combination which is securely fixed to the vertebral bone by the application of the means for securing a rod in said rod receiving channel which compression locks the rod to the flange as it simultaneously drives the staple down onto flange of the head and compression locks it thereto.

6. The vertebral body screw and staple assembly as set forth in claim 1, wherein said means for securing a rod in said rod receiving channel comprises a top locking nut which mates to a threading formed on the head portion of the screw.

7. A vertebral body screw and staple assembly for use with orthopedic rod implantation apparatus, comprising:

a vertebral body staple having a portion thereof which is flat, said flat portion having an upper surface and a lower surface, said staple further having a plurality of vertebral bone fixation protuberances extending downwardly therefrom, said flat portion further including a throughhole formed therein which extends from the upper surface through the lower surface, said throughhole having an upwardly extending annular rim and said lower surface including a concave recess around the throughhole;

first means for securing a rod in a rod receiving channel;

a vertebral body screw having a shaft portion and a rod receiving head portion, said rod receiving head portion including a lower portion and an upper portion, said upper portion having a rod receiving channel formed therein which has a lower channel surface and second means formed thereon for receiving thereon said first means for securing said rod in said rod receiving channel, said upper portion of said head portion being insertable through said throughhole of said staple from the lower surface, said lower portion of said rod receiving head portion being wider than the throughhole in the staple, such that when the staple is placed over the head of the screw only the upper portion of the head portion extends through the throughhole, and the upwardly extending annular rim of the throughhole extends above the lower channel surface of the rod receiving channel such that a rod placed in the rod receiving channel seats on the annular rim;

whereby the insertion of the screw into a vertebral bone, the placement of the staple over the head of the screw such that the vertebral bone fixation protuberances are inserted into the vertebral bone, the placement of the rod in the rod receiving channel of the head portion and onto the annular rim of the throughhole of the staple, and the application of the first means of securing the rod in the rod receiving channel of the head causes the screw, the staple, the vertebral bone and the rod to be locked together in a fully secured combination.

8. A vertebral body screw and staple assembly for use with orthopedic rod implantation apparatus, comprising:

a vertebral body staple having a throughhole formed in a surface thereof wherein the throughhole includes an annular rim which is upwardly extending, and an undersurface which forms a concave recess around the throughhole;

a vertebral body screw having a shaft and a head portion, said head portion including a rod receiving channel;

means for securing a rod in said rod receiving channel;

said staple being mountable about the head portion of said screw such that the head of the screw partially extends through the throughhole, whereby the insertion of a rod in said rod receiving channel, and the application of said means for securing the rod in the rod receiving channel causes the screw, the staple, and the rod to be locked together in a fully secured combination.

\* \* \* \* \*